United States Patent
Iida et al.

(10) Patent No.: US 9,988,342 B2
(45) Date of Patent: Jun. 5, 2018

(54) METHOD FOR PRODUCING 2-AMINOETHYLMETHACRYLATE HYDROCHLORIDE

(71) Applicant: MITSUBISHI GAS CHEMICAL COMPANY, INC., Tokyo (JP)

(72) Inventors: Yuri Iida, Niigata (JP); Masaki Takemoto, Niigata (JP); Hideyuki Sato, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days. days.

(21) Appl. No.: 15/546,479

(22) PCT Filed: Jan. 26, 2016

(86) PCT No.: PCT/JP2016/052096
§ 371 (c)(1),
(2) Date: Jul. 26, 2017

(87) PCT Pub. No.: WO2016/125623
PCT Pub. Date: Aug. 11, 2016

(65) Prior Publication Data
US 2018/0022692 A1 Jan. 25, 2018

(30) Foreign Application Priority Data

Feb. 4, 2015 (JP) ................................. 2015-020065

(51) Int. Cl.
| | |
|---|---|
| *C07C 213/02* | (2006.01) |
| *C07C 219/08* | (2006.01) |
| *C07C 69/54* | (2006.01) |
| *C07C 249/02* | (2006.01) |
| *C07C 251/24* | (2006.01) |
| *C07C 251/04* | (2006.01) |

(52) U.S. Cl.
CPC ............ *C07C 213/02* (2013.01); *C07C 69/54* (2013.01); *C07C 219/08* (2013.01); *C07C 249/02* (2013.01); *C07C 251/04* (2013.01); *C07C 251/24* (2013.01)

(58) Field of Classification Search
None
See application file for complete search history.

(56) References Cited

U.S. PATENT DOCUMENTS

| | | | |
|---|---|---|---|
| 3,037,969 A | 6/1962 | Hankins et al. | |
| 3,336,358 A | 8/1967 | McFadden | |
| 3,497,485 A * | 2/1970 | Emmons | ................... C02F 1/54 526/265 |
| 4,176,232 A | 11/1979 | Lewis et al. | |
| 4,194,052 A | 3/1980 | Lewis et al. | |
| 4,500,728 A | 2/1985 | Fazio et al. | |
| 5,185,461 A | 2/1993 | Tanaka et al. | |
| 2005/0240052 A1 | 10/2005 | Komata et al. | |
| 2013/0023694 A1 | 1/2013 | Steiger et al. | |

FOREIGN PATENT DOCUMENTS

| | | | |
|---|---|---|---|
| JP | 38-008310 | | 6/1963 |
| JP | 64-52746 | | 2/1989 |
| JP | 4-356448 | | 12/1992 |
| JP | 2001009208 | * | 1/2001 |
| JP | 4031150 | | 1/2008 |
| JP | 2013-523881 | | 6/2013 |

OTHER PUBLICATIONS

International Search Report issued in Patent Application No. PCT/JP2016/052096, dated Apr. 19, 2016.

* cited by examiner

*Primary Examiner* — Jafar Parsa
*Assistant Examiner* — Amy C Bonaparte
(74) *Attorney, Agent, or Firm* — Greenblum & Bernstein, P.L.C.

(57) ABSTRACT

Provided is a method for producing 2-aminoethyl methacrylate hydrochloride that, according to one embodiment, includes a step (A) for reacting a ketimine compound of 2-aminoethyl methacrylate with water and hydrogen chloride and obtaining a mixture containing 2-aminoethyl methacrylate hydrochloride, wherein in the step (A), the ratio of the total amount of hydrogen chloride to the total amount of ketimine compound of 2-aminoethyl methacrylate is 1.0-1.5 expressed in terms of equivalents, and the ratio of the total amount of water to the total amount of ketimine compound of 2-aminoethyl methacrylate is 1.0-2.0 expressed in terms of equivalents.

16 Claims, No Drawings

METHOD FOR PRODUCING 2-AMINOETHYLMETHACRYLATE HYDROCHLORIDE

TECHNICAL FIELD

The present invention relates to a method for producing 2-aminoethyl methacrylate hydrochloride by reacting a ketimine compound of 2-aminoethyl methacrylate with water and hydrogen chloride. 2-Aminoethyl methacrylate hydrochloride provided by the present invention is a useful compound as a raw material monomer for a polymer flocculant or coagulant, a fiber treatment agent, a modifier or a processing agent for paper, paint, ink, toner, a gluing agent, an adhesive, a chelating resin, an ion-exchange resin, a medical material, a hair care product, cosmetics, an antibacterial agent, a dispersant, a surface treatment agent, an antistatic agent, an additive for lubricating oil or fuel oil, a resist or the like.

BACKGROUND ART

Conventionally, various methods have been proposed as a method for producing 2-aminoethyl methacrylate salt. According to Patent Literatures 3 and 7, 2-aminoethyl methacrylate is generated from methacrylic acid and ethyleneimine, which is reacted with concentrated hydrochloric acid, hydrochloric acid gas or concentrated sulfuric acid to synthesize 2-aminoethyl methacrylate hydrochloride or 2-aminoethyl methacrylate sulfate. Here, 2-aminoethyl methacrylate as a reaction intermediate forms a stable salt with methacrylic acid, and methacrylic acid that once became a salt is not involved in synthesis of 2-aminoethyl methacrylate. Therefore, in order to complete the reaction, an excess amount of methacrylic acid supply is requisite with respect to the feed amount of ethyleneimine. The resulting excessive methacrylic acid supply needs to be recovered after the final step of salt exchange with hydrochloric acid or sulfuric acid, which is technically and economically disadvantageous.

Patent Literatures 4 and 5 disclose a method for obtaining solid sulfonic acid salt of 2-aminoethyl methacrylate by condensing sulfonic acid salt of monoethanolamine and methacrylic acid, but do not describe about the yield thereof.

In Patent Literature 6, 2-isopropenyl-2-oxazoline, water and hydrochloric acid are used to synthesize aminoethylmethacrylate hydrochloride but the reaction speed thereof is slow and inevitably the reaction requires a large excess amount of water in order to complete the reaction within a practical time. Accordingly, the product obtained by the method described in Patent Literature 6 will be an aqueous solution, and thus there will be additional cost in order to obtain solid 2-aminoethyl methacrylate hydrochloride like the present invention. Moreover, 2-isopropenyl-2-oxazoline as a reactant is troublesome to synthesize and thus economical rationality of this invention is again low in this sense.

Patent Literature 8 discloses reaction between hydrochloride of monoethanolamine and methacryloyl chloride, where solid 2-aminoethyl methacrylate hydrochloride is obtained.

Patent Literature 9 discloses reaction between hydrochloride of monoethanolamine and methacrylic anhydride, where solid 2-aminoethyl methacrylate hydrochloride is obtained.

However, methacryloyl chloride and methacrylic anhydride that are used as raw materials in Patent Literatures 8 and 9 are generally difficult to handle and expensive, and thus unsuitable to be used as raw materials in an industrial process that assumes certain production quantity.

Patent Literature 1 discloses a method in which Schiff base obtained by reacting monoethanolamine and methyl isobutyl ketone is reacted with methyl methacrylate or methyl acrylate to synthesize 2-aminoethyl methacrylate methyl isobutyl ketimine or 2-aminoethyl acrylate methyl isobutyl ketimine, and then this compound is dissolved in water, cooled to 0-5° C. and added with an aqueous phosphoric or acetic acid solution.

Moreover, Patent Literature 2 discloses a method in which an aqueous hydrochloric acid solution is added to 2-aminoethyl methacrylate methyl ethyl ketimine at 25° C. According to these methods, however, the compound of interest, that is, 2-aminoethyl methacrylate hydrochloride, was difficult to be isolated with a good yield.

CITATION LIST

Patent Literatures

Patent Literature 1: U.S. Pat. No. 3,037,969
Patent Literature 2: Japanese Patent No. 4031150
Patent Literature 3: U.S. Pat. No. 3,336,358
Patent Literature 4: U.S. Pat. No. 4,176,232
Patent Literature 5: U.S. Pat. No. 4,194,052
Patent Literature 6: U.S. Pat. No. 4,500,728
Patent Literature 7: Japanese Unexamined Patent Application Publication No. Heisei 4-356448
Patent Literature 8: US Patent Application Publication No. 2005/0240052A1
Patent Literature 9: Japanese Unexamined Patent Application Publication (Translation of PCT) No. 2013-523881

SUMMARY

Technical Problem

As described above, Patent Literature 2 and else mentioned above describe a method for producing 2-aminoethyl methacrylate hydrochloride represented by Formula (3) below by reacting a ketimine compound of 2-aminoethyl methacrylate represented by Formula (1) or (2) below with water and an acid (organic or inorganic acid).

According to the method described in Patent Literature 2 and else, however, side reaction may occur and by-products (impurities) may be generated during the process of synthesizing the compound represented by Formula (3) that has multiple characteristic functional groups. If such by-products (impurities) are contained or if a large amount of unreacted raw material remains in the reaction system, it would be very difficult to separate/purify the compound of interest represented by Formula (3) considering polymerizability, thermal stability and/or hygroscopicity of the compound of interest. Furthermore, if the content of the above-described by-products (impurities) or the unreacted raw material in the reaction product is large, there is a problem that the polymerization degree cannot be increased upon further polymerizing the compound represented by Formula (3). Moreover, if the reaction product is to be used as a raw material for other fine synthesis, the reaction thereof may possibly be hindered. Thus, a method for obtaining a compound represented by General formula (3) below with a high purity and a high yield has been in demand.

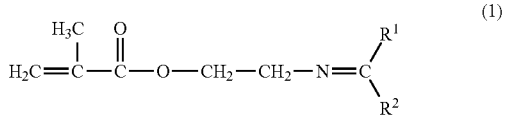

Wherein, in Formula (1), $R^1$ and $R^2$ each independently represent an alkyl group or an aryl group with a carbon number of 1-12.

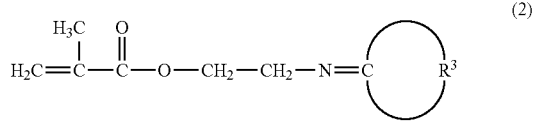

Wherein, in Formula (2), $R^3$ represents a bivalent hydrocarbon group with a carbon number of 3-10 that forms a ring with a carbon atom to which it binds, and may partly have a double bond.

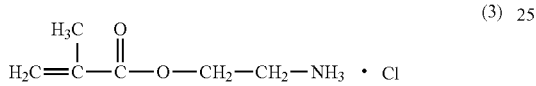

Solution to Problem

The present inventors have gone through keen studies in order to solve the above-described problem, as a result of which found that 2-aminoethyl methacrylate hydrochloride represented by Formula (3) can be obtained with a high purity and a high yield by controlling the feed amount ratios of water and hydrogen chloride to a ketimine compound of 2-aminoethyl methacrylate to lie within a specific range upon a step of reacting the ketimine compound of 2-aminoethyl methacrylate represented by Formula (1) or (2) with water and hydrogen chloride for producing 2-aminoethyl methacrylate hydrochloride represented by Formula (3), thereby accomplishing the present invention. Thus, the present invention is as follows.

[1] A method for producing 2-aminoethyl methacrylate hydrochloride, comprising Step (A) of reacting a ketimine compound of 2-aminoethyl methacrylate represented by Formula (1) or (2) below,

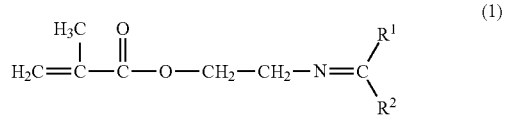

wherein, in Formula (1), $R^1$ and $R^2$ each independently represent an alkyl group or an aryl group with a carbon number of 1-12,

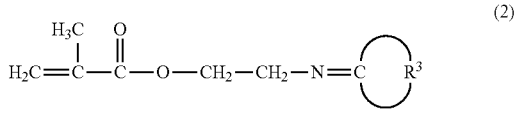

wherein, in Formula (2), $R^3$ represents a bivalent hydrocarbon group with a carbon number of 3-10 that forms a ring with a carbon atom to which it binds, and may partly have a double bond, with water and hydrogen chloride to obtain a mixture containing 2-aminoethyl methacrylate hydrochloride represented by Formula (3) below,

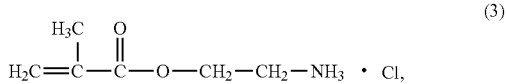

wherein, in Step (A), the ratio of the whole amount of hydrogen chloride to the whole amount of the ketimine compound of 2-aminoethyl methacrylate is in a range of 1.0-1.5 in equivalent ratio, and the ratio of the whole amount of water to the whole amount of the ketimine compound of 2-aminoethyl methacrylate is in a range of 1.0-2.0 in equivalent ratio.

[2] The method for producing 2-aminoethyl methacrylate hydrochloride according to [1], wherein $R^1$ and $R^2$ in Formula (1) above each independently represent an alkyl group with a carbon number of 1-4.

[3] The method for producing 2-aminoethyl methacrylate hydrochloride according to [2], wherein, in Formula (1) above, $R^1$ represents a methyl group and $R^2$ represents an ethyl group or an isobutyl group.

[4] The method for producing 2-aminoethyl methacrylate hydrochloride according to [3], wherein $R^2$ in Formula (1) above represents an isobutyl group.

[5] The method for producing 2-aminoethyl methacrylate hydrochloride according to [3], wherein $R^2$ in Formula (1) above represents an ethyl group.

[6] The method for producing 2-aminoethyl methacrylate hydrochloride according to any one of [1]-[5], wherein hydrogen chloride is hydrogen chloride gas.

[6-1] The method for producing 2-aminoethyl methacrylate hydrochloride according to any one of [1]-[6], wherein the reaction of the ketimine compound of 2-aminoethyl methacrylate represented by Formula (1) with water and hydrogen chloride is carried out by simultaneously supplying the ketimine compound of 2-aminoethyl methacrylate represented by Formula (1) or (2) and hydrogen chloride gas to water or a mixture of water and an organic solvent.

[6-2] The method for producing 2-aminoethyl methacrylate hydrochloride according to any one of [1]-[6], wherein the reaction of the ketimine compound of 2-aminoethyl methacrylate represented by Formula (1) with water and hydrogen chloride is carried out by supplying hydrogen chloride gas to a mixture containing water, the ketimine compound of 2-aminoethyl methacrylate represented by General formula (1) or (2) and optionally an organic solvent.

[6-3] The method for producing 2-aminoethyl methacrylate hydrochloride according to any one of [1]-[6], the reaction of the ketimine compound of 2-aminoethyl methacrylate represented by Formula (1) with water and hydrogen chloride is carried out by feeding a part of a reaction raw material containing water, hydrogen chloride (hydrochloric acid) and the ketimine compound of 2-aminoethyl methacrylate represented by Formula (1) or (2) into a reaction vessel in advance and thereafter supplying the rest of the reaction raw material.

[7] The method for producing 2-aminoethyl methacrylate hydrochloride according to any one of [1]-[6-3], wherein the reaction of the ketimine compound of 2-aminoethyl methacrylate represented by Formula (1) with water and hydrogen chloride is carried out such that the ratio of the accumulated supply amount of hydrogen chloride to the accumulated supply amount of the ketimine compound of 2-aminoethyl methacrylate is maintained at 1.0 or higher in equivalent ratio throughout the whole period from the starting point of mixing hydrogen chloride with the ketimine compound of 2-aminoethyl methacrylate to the end point of mixing the whole amount of hydrogen chloride.

[7-1] The method for producing 2-aminoethyl methacrylate hydrochloride according to [7], wherein the ketimine compound of 2-aminoethyl methacrylate represented by Formula (1) is 2-aminoethylmethacrylate methyl ethyl ketimine.

[8] The method for producing 2-aminoethyl methacrylate hydrochloride according to any one of [1]-[7-1], wherein the reaction of the ketimine compound of 2-aminoethyl methacrylate with water and hydrogen chloride is carried out in the presence of at least one organic solvent selected from the group consisting of tetrahydrofuran, methyl isobutyl ketone, methyl ethyl ketone, acetone and dioxane.

[9] The method for producing 2-aminoethyl methacrylate hydrochloride according to [8], wherein the organic solvent is at least one selected from the group consisting of methyl isobutyl ketone and methyl ethyl ketone.

[10] The method for producing 2-aminoethyl methacrylate hydrochloride according to either one of [8] and [9], wherein the organic solvent is used in an amount four times as much as or less than the amount of the ketimine compound of 2-aminoethyl methacrylate represented by Formula (1) or (2) above in weight ratio.

[11] The method for producing 2-aminoethyl methacrylate hydrochloride according to any one of [1]-[10], wherein the temperature in Step (A) is controlled to lie in a range of −10-60° C. from the starting point of supplying the reaction raw material in the reaction vessel to the end point of supplying the reaction raw material.

[12] The method for producing 2-aminoethyl methacrylate hydrochloride according to any one of [1]-[11], wherein the temperature in Step (A) is controlled to lie in a range of −10-40° C. from the end point of supplying the reaction raw material to the end point of the reaction.

[13] The method for producing 2-aminoethyl methacrylate hydrochloride according to any one of [1]-[12], further comprising Step (B) which comprises Step (b1) of separating solid precipitate from the mixture containing 2-aminoethyl methacrylate hydrochloride obtained in Step (A); Step (b2) of washing the solid precipitate with a solvent; and Step (b3) of drying the washed solid precipitate.

[14] The method for producing 2-aminoethyl methacrylate hydrochloride according to [13], wherein the solvent in Step (b2) is at least one selected from the group consisting of acetone, methyl ethyl ketone, methyl isobutyl ketone, tetrahydrofuran and 1,4-dioxane.

[15] The method for producing 2-aminoethyl methacrylate hydrochloride according to either one of [13] and [14], wherein the solvent in Step (b2) contains a polymerization inhibitor.

[16] The method for producing 2-aminoethyl methacrylate hydrochloride according to any one of [1]-[15], wherein 2-aminoethyl methacrylate hydrochloride is solid.

[16-1] The method for producing 2-aminoethyl methacrylate hydrochloride according to any one of [1]-[16], wherein 2-aminoethyl methacrylate hydrochloride can be obtained with a yield of 65% or higher.

[16-2] The method for producing 2-aminoethyl methacrylate hydrochloride according to any one of [1]-[16-1], wherein 2-aminoethyl methacrylate hydrochloride has a purity of 88% or higher.

In addition, the following aspects described in Japanese Patent Application No. 2015-20065 based on which the present application claims priority are also within the scope of the present invention.

[1'] A method for producing 2-aminoethyl methacrylate hydrochloride, comprising Step (A) of reacting a ketimine compound of 2-aminoethyl methacrylate represented by Formula (1) or (2) below, $$H_2C=C(CH_3)-C(=O)-O-CH_2-CH_2-N=C(R^1)(R^2) \quad (1)$$

wherein, in Formula (1), $R^1$ and $R^2$ represent an alkyl group or an aryl group with a carbon number of 1-12;

$$H_2C=C(CH_3)-C(=O)-O-CH_2-CH_2-N=C\langle R^3\rangle \quad (2)$$

wherein, in Formula (2), $R^3$ represents a bivalent hydrocarbon group with a carbon number of 3-10, and may partly have a double bond;
with water and hydrogen chloride to obtain a mixture containing 2-aminoethyl methacrylate hydrochloride represented by Formula (3) below, $$H_2C=C(CH_3)-C(=O)-O-CH_2-CH_2-NH_3 \cdot Cl, \quad (3)$$

wherein, in Step (A), the ratio of the whole amount of hydrogen chloride to the whole amount of the ketimine compound of 2-aminoethyl methacrylate subjected to the reaction is in a range of 1.0-1.5 in equivalent ratio, and the ratio of the whole amount of water to the whole amount of the ketimine compound of 2-aminoethyl methacrylate is in a range of 1.0-2.0 in equivalent ratio.

[2'] The method for producing 2-aminoethyl methacrylate hydrochloride according to [1'], wherein, in Formula (1), $R^1$ represents a methyl group and $R^2$ represents an ethyl group or a 2-methylpropyl group.

[3'] The method for producing 2-aminoethyl methacrylate hydrochloride according to [2'], wherein, in Formula (1), $R^2$ represents a 2-methylpropyl group.

[4'] The method for producing 2-aminoethyl methacrylate hydrochloride according to [2'], wherein, in Formula (1), $R^2$ represents an ethyl group.

[5'] The method for producing 2-aminoethyl methacrylate hydrochloride according to [4'], wherein the ketimine compound of 2-aminoethyl methacrylate represented by Formula (1) is mixed with hydrogen chloride for the reaction such that the ratio of the accumulated supply amount of hydrogen chloride to the accumulated supply amount of the ketimine compound of 2-aminoethyl methacrylate is 1.0 or higher in equivalent ratio throughout the whole period from the starting point of mixing hydrogen chloride and water with the ketimine compound of 2-aminoethyl methacrylate to the end point of mixing the whole amount of hydrogen chloride and water.

[6'] The method for producing 2-aminoethyl methacrylate hydrochloride according to any one of [1']-[5'], wherein, in Step (A), the ketimine compound of 2-aminoethyl methacrylate is reacted with water and hydrogen chloride in the presence of at least one organic solvent selected from tetrahydrofuran, methyl isobutyl ketone, methyl ethyl ketone, acetone and dioxane.

[7'] The method for producing 2-aminoethyl methacrylate hydrochloride according to [6'], wherein the organic solvent is at least one selected from methyl isobutyl ketone and methyl ethyl ketone.

[8'] The method for producing 2-aminoethyl methacrylate hydrochloride according to any one of [1']-[7'], wherein the organic solvent, in Step (A), is used in an amount four times as much as or less than the amount of the ketimine compound of 2-aminoethyl methacrylate represented by Formula (1) or (2) above in weight ratio.

[9'] The method for producing 2-aminoethyl methacrylate hydrochloride according to any one of [1']-[8'], wherein the reaction temperature in Step (A) is controlled to lie in a range of −10-60° C. from the starting point of supplying the reaction raw material in the reaction vessel to the end point of supplying the reaction raw material.

[10'] The method for producing 2-aminoethyl methacrylate hydrochloride according to any one of [1']-[9'], wherein the reaction temperature in Step (A) is controlled to lie in a range of −10-40° C. from the end point of supplying the reaction raw material to the end point of the reaction.

[11'] The method for producing 2-aminoethyl methacrylate hydrochloride according to any one of [1']-[10'], further comprising Step (B) which comprises Step (b1) of separating solid precipitate from the mixture containing 2-aminoethyl methacrylate hydrochloride; Step (b2) of washing the solid precipitate with a solvent; and Step (b3) of drying the washed solid precipitate.

[12'] The method for producing 2-aminoethyl methacrylate hydrochloride according to any one of [1']-[11'], wherein the solvent in Step (b2) is at least one selected from acetone, methyl ethyl ketone, methyl isobutyl ketone, tetrahydrofuran and 1,4-dioxane.

[13'] The method for producing 2-aminoethyl methacrylate hydrochloride according to any one of [1']-[12'], wherein the solvent in Step (b2) is mixed with a polymerization inhibitor.

Advantageous Effects of Invention

By carrying out the present invention, conversion from a ketimine compound of 2-aminoethyl methacrylate represented by Formula (1) or (2) to 2-aminoethyl methacrylate hydrochloride represented by Formula (3) can be proceeded with little side reaction. As a result, 2-aminoethyl methacrylate hydrochloride represented by Formula (3), i.e., a compound of interest of the present invention, can stably be produced in a solid state with a high purity and a high yield. 2-Aminoethyl methacrylate hydrochloride, i.e., the compound of interest of the present invention, obtained in a solid state with a high purity can not only be used as an additive such as a polymer flocculant or coagulant, a fiber treatment agent, a modifier or a processing agent for paper, paint, ink, toner, a gluing agent, an adhesive, a chelating resin, an ion-exchange resin, a medical material, a hair care product, cosmetics, an antibacterial agent, a dispersant, a surface treatment agent, an antistatic agent, lubricating oil or fuel oil as mentioned previously but it can also be utilized in fine synthesis in which an organic compound is obtained by further derivatizing 2-aminoethyl methacrylate hydrochloride. For example, it can be applied in the field of electronic materials, for example, as a raw material for a resist, which is industrially significant.

DESCRIPTION OF EMBODIMENTS

Hereinafter, embodiments of the present invention will be described in detail.

One embodiment of the present invention provides a method for producing 2-aminoethyl methacrylate hydrochloride, the method comprising Step (A) of reacting a ketimine compound of 2-aminoethyl methacrylate represented by Formula (1) or (2) below with water and hydrogen chloride to obtain a mixture containing 2-aminoethyl methacrylate hydrochloride represented by Formula (3) below. Here, in Step (A), the ratio of the whole amount of hydrogen chloride to the whole amount of the ketimine compound of 2-aminoethyl methacrylate is in a range of 1.0-1.5 in equivalent ratio, and the ratio of the whole amount of water to the whole amount of the ketimine compound of 2-aminoethyl methacrylate is in a range of 1.0-2.0 in equivalent ratio:

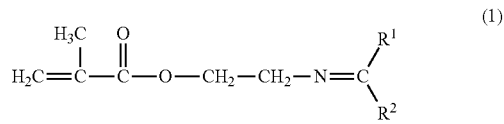

wherein, in Formula (1), $R^1$ and $R^2$ each independently represent an alkyl group or an aryl group with a carbon number of 1-12;

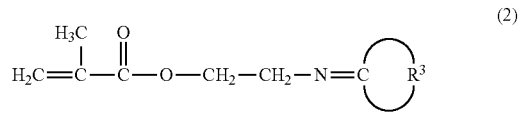

wherein, in Formula (2), $R^3$ represents a bivalent hydrocarbon group with a carbon number of 3-10 that forms a ring with a carbon atom to which it binds, and may partly have a double bond),

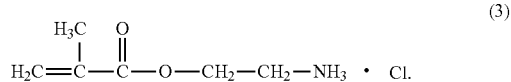

According to the above-described embodiment, by controlling the feed amount ratios of water and hydrogen chloride to the ketimine compound of 2-aminoethyl methacrylate to lie within the above-mentioned ranges, 2-aminoethyl methacrylate hydrochloride represented by Formula (3) can be obtained in a solid state with a high purity and a high yield. The phrase "obtained in a solid state" means that 2-aminoethyl methacrylate hydrochloride is present as white crystals in the mixture obtained by this embodiment.

Although the reason why the compound of interest can be obtained in a solid state with a high purity and a high yield by making the feed amounts of water and hydrogen chloride to lie in the above-mentioned ranges is uncertain, it can be presumed as follows. Specifically, in a case where the feed amount of hydrogen chloride exceeds the above-mentioned range, the excessive acid suppresses the deprotection reaction which is a phenomenon specific to the reaction of the present invention and thus it takes a long time to complete the reaction. Therefore, if 2-aminoethyl methacrylate hydrochloride is separated, washed and dried before the reaction is complete, the unreacted ketimine compound of 2-aminoethyl methacrylate is incorporated into the crystals, thereby lowering the purity of 2-aminoethyl methacrylate hydrochloride. Moreover, due to the remaining unreacted ketimine compound of 2-aminoethyl methacrylate, the concentration of 2-aminoethyl methacrylate hydrochloride to the organic solvent and ketone resulting from deprotection decreases, which lowers the isolation yield than expected. On the other hand, in a case where the feed amount of hydrogen chloride falls below the above-mentioned range, the excessive ketimine compound of 2-aminoethyl methacrylate represented by Formula (1) or (2) could not take a form of hydrochloride, and therefore not only the raw material is wasted but also the purity of the compound of interest is decreased due to the unreacted ketimine compound of 2-aminoethyl methacrylate.

Meanwhile, in a case where the feed amount of water falls below the above-mentioned range, a part of the ketimine compound of 2-aminoethyl methacrylate represented by Formula (1) or (2) cannot contribute to the deprotection reaction with water, and thus not only the raw material is wasted but also the purity of the compound of interest is decreased. On the other hand, in a case where the feed amount of water exceeds the above-mentioned range, the excessive water will dissolve 2-aminoethyl methacrylate hydrochloride represented by Formula (3), and thus not only the isolation yield is extremely decreased but also water along with impurities will intrude into the crystals of 2-aminoethyl methacrylate hydrochloride, thereby decreasing the purity of the product.

In Formula (1), $R^1$ and $R^2$ each independently represent an alkyl group or an aryl group with a carbon number of 1-12, preferably an alkyl group with a carbon number of 1-4. Specific examples include a methyl group, an ethyl group, a propyl group and an isobutyl group, where it is preferably a methyl group, an ethyl group or an isobutyl group. In particular, in a preferable aspect, either one of $R^1$ and $R^2$ is a methyl group while the other is an ethyl group or an isobutyl group.

In Formula (2), $R^3$ represents a bivalent hydrocarbon group with a carbon number of 3-10 that forms a ring with a carbon atom to which it binds, and may partly have a double bond. The carbon number is preferably 4-7 and more preferably 5-6. The number of the double bond is 0-2, preferably 0-1 and more preferably 0. Specifically, the ring formed by $R^3$ and the carbon atom to which it binds is cyclopentane, cyclohexane, 2-cyclopentene, 2-cyclohexene, 2,4-cyclopentadiene or 2,5-cyclohexadiene, and preferably cyclopentane or cyclohexane.

Furthermore, as the ketimine compound of 2-aminoethyl methacrylate, a compound represented by Formula (1) is preferably used among the compounds represented by Formula (1) and Formula (2).

The ketimine compound of 2-aminoethyl methacrylate represented by Formula (1) or (2) used as a raw material can be obtained through transesterification reaction of so-called Schiff base, i.e., a compound obtained by reacting 2-aminoethanol with ketone represented by Formula (4) or (5) below (a compound represented by Formula (6) or (7) below), and methacrylate ester. Specific examples of the ketone represented by Formula (4) or (5) include acetone, methyl ethyl ketone, methyl propyl ketone, methyl isobutyl ketone, methyl isopropyl ketone, diisobutyl ketone, cyclopentanone and cyclohexanone. Among the above-mentioned compounds, methyl ethyl ketone or methyl isobutyl ketone is preferable considering availability, easiness of synthesis of Schiff base and easiness of purification of the resulting compound.

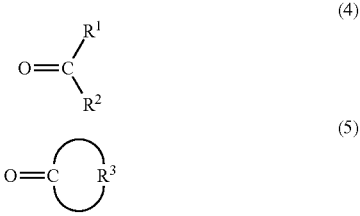

Wherein, $R^1$ and $R^2$ in Formula (4) and $R^3$ in Formula (5) are as defined in Formulae (1) and (2) above.

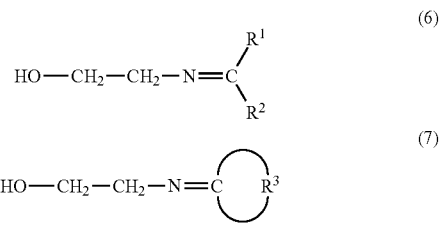

Wherein, $R^1$ and $R^2$ in Formula (6) and $R^3$ in Formula (7) are as defined in Formulae (1) and (2) above.

A method for synthesizing 2-aminoethyl methacrylate represented by Formula (1) or (2) used as a raw material may be transesterification reaction of so-called Schiff base, i.e., a compound represented by Formula (6) or (7), and methacrylate ester. As methacrylate ester, compounds of various structures may be used, where specific examples include methyl methacrylate, ethyl methacrylate, n-butyl methacrylate and isobutyl methacrylate. Taking availability into consideration, methyl methacrylate is most preferable.

The transesterification reaction of the so-called Schiff base, i.e., a compound represented by Formula (6) or Formula (7), and methacrylate ester is not particularly limited and a certain known catalyst can be used. For example, it may be obtained by a known method, for example, a method in which alcohol as a by-product is drawn out from the system by reactive distillation while heating under reflux, in the presence of sodium alcoholate, magnesium alcoholate, titanium alcoholate, dibutyltin oxide, a zinc acetylacetone complex or the like. A ketimine compound of 2-aminoethyl methacrylate represented by Formula (1) or (2) resulting from this reaction can be purified by a common technique such as distillation, extraction, recrystallization or the like.

<Step (A)>

Hereinafter, Step (A) will be described.

Step (A) is a step for obtaining a mixture containing 2-aminoethyl methacrylate hydrochloride represented by Formula (3) by reacting a ketimine compound of 2-aminoethyl methacrylate represented by Formula (1) or (2) with water and hydrogen chloride.

A ketimine compound of 2-aminoethyl methacrylate represented by Formula (1) or (2) is mixed with hydrogen chloride and water in the presence or absence of an organic solvent so that ketone is first liberated through reaction with water, thereby obtaining 2-aminoethyl methacrylate. Immediately after that, it is subjected to neutralization reaction with hydrogen chloride and converted into 2-aminoethyl methacrylate hydrochloride represented by Formula (3), i.e., the compound of interest. Through the above-described reaction, a mixture containing 2-aminoethyl methacrylate hydrochloride represented by Formula (3) as the main component is obtained. Hereinafter, Step (A) is sometimes referred to as a deprotection/neutralization reaction step.

For carrying out the deprotection/neutralization reaction step, various methods may be suggested as the method for mixing the ketimine compound of 2-aminoethyl methacrylate represented by Formula (1) or (2) with hydrogen chloride and water. For example: 1. a method in which a ketimine compound of 2-aminoethyl methacrylate represented by Formula (1) or (2) and hydrogen chloride gas are simultaneously supplied to a prescribed amount of water or a prescribed amount of a mixture of water and an organic solvent; 2. a method in a ketimine compound of 2-aminoethyl methacrylate represented by General formula (1) or (2) is added to a prescribed amount of a mixture of water, hydrogen chloride (hydrochloric acid) and an organic solvent; 3. a method in which hydrogen chloride gas is supplied to a prescribed amount of a mixture of water and a ketimine compound of 2-aminoethyl methacrylate represented by General formula (1) or (2) or said mixture that is further added with an organic solvent; and 4. a method in which an organic solvent containing a prescribed amount of hydrogen chloride (hydrochloric acid) and a ketimine compound of 2-aminoethyl methacrylate represented by Formula (1) or (2) are simultaneously supplied to a prescribed amount of water. Examples of various methods also include: 5. a method in which a prescribed amount of a part of water and/or hydrogen chloride (hydrochloric acid) and/or a ketimine compound of 2-aminoethyl methacrylate represented by Formula (1) or (2) is fed into a reaction vessel in advance, and then the rest of water and/or hydrogen chloride (hydrochloric acid) and/or a ketimine compound of 2-aminoethyl methacrylate represented by Formula (1) or (2) are supplied; and 6. a method in which a prescribed amount of water, a prescribed amount of hydrogen chloride (hydrochloric acid) and a ketimine compound of 2-aminoethyl methacrylate represented by Formula (1) or (2), and if necessary an organic solvent are sequentially supplied to a supply pipe that communicates the reaction raw materials so that they are mixed in the reaction raw material supply pipe. Any method for mixing the raw materials may be employed as long as the ketimine compound of 2-aminoethyl methacrylate, hydrogen chloride and water can be mixed.

When the ketimine compound of 2-aminoethyl methacrylate represented by Formula (1) or (2) is mixed with hydrogen chloride and water, the ratio of the accumulated supply amount of hydrogen chloride to the accumulated supply amount of the ketimine compound is preferably maintained at 1.0 or higher in equivalent ratio throughout the whole period from the starting point of mixing hydrogen chloride with the ketimine compound to the end point of mixing the whole amount of hydrogen chloride. Such a mixing aspect is especially suitable when a compound wherein $R^1$ is a methyl group and $R^2$ is an ethyl group (namely, 2-aminoethyl methacrylate methyl ethyl ketimine) is used as the ketimine compound. This is because when 2-aminoethyl methacrylate methyl ethyl ketimine is used, decreases in the yield and the purity are likely to be suppressed.

Herein, the accumulated supply amount of the ketimine compound or hydrogen chloride refers to the total amount of the ketimine compound or hydrogen chloride supplied up to a certain time point between the starting point of mixing and the end point of mixing. The ratio of the accumulated supply amount of hydrogen chloride to the accumulated supply amount of the ketimine compound is maintained preferably at 1.0 or higher in equivalent ratio, more preferably in a range of 1.0-1.5 in equivalent ratio, more preferably in a range of 1.0-1.2 in equivalent ratio and particularly preferably in a range of 1.00-1.05.

The form of hydrogen chloride subjected to the above-described deprotection/neutralization reaction step may take any form such as gas, an aqueous solution or an organic solvent solution. In order to add hydrogen chloride and water in an amount (equivalent ratio) described in detail below, hydrogen chloride gas is preferably employed. Specifically, in the method according to this embodiment, hydrogen chloride and water are preferably added in an equivalent ratio close to 1:1 and therefore the amount of water needs to be considered if hydrogen chloride is added in a form of an aqueous solution. Moreover, if hydrogen chloride is added in a form of an organic solvent, addition of hydrogen chloride in a favorable equivalent ratio would increase the amount of the liquid component in the system. As a result, volume efficiency with respect to the yield of the resulting 2-aminoethyl methacrylate hydrochloride decreases, which is economically disadvantageous. On the other hand, use of hydrogen chloride gas easies addition of hydrogen chloride and water at an equivalent ratio close to 1:1, lessens the amount of the liquid component in the system, and enhances the volume efficiency with respect to 2-aminoethyl methacrylate hydrochloride. Therefore, use of hydrogen chloride gas is advantageous for efficiently obtaining a compound of interest, i.e., 2-aminoethyl methacrylate hydrochloride, in a solid state.

The equivalent ratio of hydrogen chloride and water (hydrogen chloride/water) may be 1.0/2.0, 1.0/1.5 or 1.0/1.2 where the ratio of water is larger, or may be 1.5/1.0, 1.2/1.0 or 1.0/1.0 where the ratio of hydrogen chloride is larger or they are in an exact equivalent. Accordingly, hydrogen chloride and water may be at any equivalent ratio regardless of which of hydrogen chloride or water should be in a larger amount as long as it lies within the equivalent ratio of hydrogen chloride and water defined herein.

With regard to the description of the equivalent ratio of hydrogen chloride, the amount (or the whole amount) of hydrogen chloride refers to the total amount of whole hydrogen chloride existing in the reaction system. Therefore, if hydrogen chloride is added in various forms (for example, a combination of hydrochloric acid and hydrogen chloride gas), it refers to the total amount of undiluted (i.e., 100%) hydrogen chloride contained in these various forms. Moreover, with regard to the description of equivalent ratio of water, the amount (or the whole amount) of water refers to the total amount of whole water existing in the reaction system. Therefore, if a raw material is added as an aqueous solution (for example, if hydrogen chloride is added as hydrochloric acid, if a polymerization inhibitor is added as an aqueous solution, etc.), it refers to the total amount of water including water of the solvent.

The amount of hydrogen chloride used with respect to a ketimine compound of 2-aminoethyl methacrylate represented by Formula (1) or (2) needs to accurately be controlled. Specifically, the ratio of the whole amount of hydrogen chloride subjected to the above-described deprotection/neutralization reaction step to the whole amount of the ketimine compound of 2-aminoethyl methacrylate represented by Formula (1) or (2) subjected to said deprotection/neutralization reaction step is preferably in a range of 1.0-1.5 in equivalent ratio (equivalent of hydrogen chloride/equivalent of ketimine compound of 2-aminoethyl methacrylate). If the equivalent ratio is in the above-mentioned range, the yield and/or the purity of the compound of interest, i.e., 2-aminoethyl methacrylate hydrochloride, can be enhanced. On the other hand, if the equivalent ratio is lower than 1.0, the excessive ketimine compound of 2-aminoethyl methacrylate represented by Formula (1) or (2) that cannot form hydrochloride remains in a large amount, which is not only a waste of the raw material but also causes decrease in the purity of the compound of interest. Moreover, if the equivalent ratio exceeds 1.5, the excessive acid suppresses the deprotection reaction, which may cause a phenomenon of taking a very long time to complete the reaction. If the equivalent ratio is lower than 1.2, the yield and the purity of the compound of interest is enhanced as compared to a case where the equivalent ratio is 1.5. In particular, if the equivalent ratio is 1.05 or lower, the compound of interest, i.e., 2-aminoethyl methacrylate hydrochloride represented by Formula (3), can be obtained with an extremely high purity and high yield. Accordingly, the amount of hydrogen chloride that is preferable for carrying out the method of the embodiment is such that the ratio of hydrogen chloride to the ketimine compound of 2-aminoethyl methacrylate represented by Formula (1) or (2) is preferably in a range of 1.0-1.2 and more preferably in a range of 1.00-1.05 in equivalent ratio.

Additionally, the amount of water used in the above-described deprotection/neutralization reaction step also needs to accurately be controlled. Specifically, the amount of water subjected to the deprotection/neutralization reaction step is such that the equivalent ratio of water to the ketimine compound of 2-aminoethyl methacrylate represented by Formula (1) or (2) (equivalent of water/equivalent of ketimine compound of 2-aminoethyl methacrylate) is preferably in a range of 1.0-2.0. If the equivalent ratio is in the above-mentioned range, the yield and/or the purity of the compound of interest, i.e., 2-aminoethyl methacrylate hydrochloride, is enhanced. The equivalent ratio is in a range of more preferably 1.0-1.5, still more preferably 1.0-1.2 and most preferably 1.00-1.05.

If the equivalent ratio of water to the compound represented by Formula (1) or (2) is lower than 1.0, a part of the compound represented by Formula (1) or (2) cannot contribute to the deprotection reaction with water, which is not only a waste of the raw material but also causes decrease in purity of the compound of interest. Moreover, if the equivalent ratio of water to the compound represented by Formula (1) or (2) exceeds 2.0, the excessive water will dissolve 2-aminoethyl methacrylate hydrochloride represented by Formula (3) and thus the isolation yield of the compound of interest is extremely decreased. Furthermore, since impurities intrudes into the crystals of 2-aminoethyl methacrylate hydrochloride, the purity of the product will be decreased. Meanwhile, if the equivalent ratio of water is 1.5, the yield is improved as compared to the case where the equivalent ratio is 2.0 but the purity of the compound of interest, i.e., 2-aminoethyl methacrylate hydrochloride, is limited to about 95%. If the equivalent ratio of water is 1.2, 2-aminoethyl methacrylate hydrochloride with a yield of 90% or higher and a purity of 99% or higher can be obtained. Furthermore, if the amount of water used is reduced to the equivalent ratio of 1.05 or 1.01 with an appropriate amount of hydrogen chloride used, solid 2-aminoethyl methacrylate hydrochloride with a purity of 99% or higher can be obtained substantially quantitatively.

An organic solvent may be used as the reaction solvent in the deprotection/neutralization reaction step. Examples of the conditions of the organic solvent used include that it has the capacity of dissolving water for 2 wt % or more, that it has no active hydroxy group and that it does not dissolve 2-aminoethyl methacrylate hydrochloride for more than 1 wt %. Examples of the organic solvent include at least one type of compound selected from ketone represented by Formula (4) or (5) above, tetrahydrofuran and dioxane. These compounds may be used in combination. Among them, methyl isobutyl ketone, methyl ethyl ketone or acetone is preferable. Among the ketones represented by Formula (4) or (5) above, a compound that is the same as a ketone used for synthesizing Schiff base by reacting with 2-aminoethanol may be used.

The amount of the organic solvent used is preferably four times or less in weight ratio with respect to the ketimine compound of 2-aminoethyl methacrylate represented by Formula (1) or (2) that is used as the raw material. It is preferably 0-4 times, and particularly preferably 3-4 times. If the amount exceeds four times, the production efficiency is deteriorated and a large amount of organic solvent needs to be recovered. Moreover, there is no problem in using, as the organic solvent, a compound that is the same as a ketone represented by Formula (4) or (5) used for synthesizing Schiff base by reacting with 2-aminoethanol.

The above-described deprotection/neutralization reaction is preferably carried out in a predetermined reaction temperature range. The reaction temperature as used herein refers to the temperature of the reaction mixture. From the perspective of controlling the reaction temperature, the above-described deprotection/neutralization reaction step can be divided into a raw material pouring step and a maturation step as described below, where the reaction temperatures are preferably independently controlled in the raw material pouring step and the maturation step, respectively.

(Definition of Raw Material Pouring Step)

In a case where the above-described deprotection/neutralization reaction step is carried out using a reaction vessel, the raw material pouring step refers to a phase from the starting point of supplying the reaction raw material that is to be subjected to the synthesis of 2-aminoethyl methacrylate hydrochloride represented by Formula (3) into the reaction vessel to the end point of supplying the reaction raw material. The reaction raw material contains a ketimine compound of 2-aminoethyl methacrylate represented by Formula (1) or (2), hydrogen chloride and water. The reaction raw material may contain an organic solvent that is used as a reaction solvent. The method for supplying the reaction raw material into the reaction vessel is as described above. Since the raw material pouring step generates a large quantity of neutralization heat due to the mixing of an acid and a base, cooling is encouraged. A preferable reaction temperature range in the raw material pouring step is generally −10-60° C., preferably −10-40° C. and more preferably −10-20° C.

(Definition of Maturation Step)

The maturation step refers to a step of stirring the reaction solution at a constant temperature during a phase from the end point of supplying the reaction raw material to the end point of the reaction. The end point of the reaction in this maturation step refers to a time point where extinction of the ketimine compound of 2-aminoethyl methacrylate can be confirmed by analyzing the reaction solution by gas chromatography. While there is slight heat generation in the maturation step, it is important to maintain the reaction temperature to be substantially constant and stirring is also important since a large amount of crystals precipitate. A preferable reaction temperature range in the maturation step is generally −10-40° C. and preferably −10-20° C. In either of the raw material pouring step and the maturation step, the reaction speed is reduced and thus efficiency is deteriorated if the reaction temperature is lower than −10° C. while a side reaction such as polymerization reaction is likely to occur if the reaction temperature exceeds 40° C.

<Step (B)>

2-Aminoethyl methacrylate hydrochloride represented by Formula (3) produced in the above-described deprotection/neutralization reaction step exists as white crystals, at the end of the reaction, in the mixture containing 2-aminoethyl methacrylate hydrochloride as the main component. Step (B) described herein refers to a step of separating/purifying solid 2-aminoethyl methacrylate hydrochloride of interest represented by Formula (3) from this mixture, where Step (B) includes Step (b1) of separating the solid precipitate from the mixture obtained in Step (A), Step (b2) of washing the solid precipitate, and Step (b3) of drying the washed solid precipitate.

As the method for separating the solid precipitate from the mixture containing 2-aminoethyl methacrylate hydrochloride as the main component in Step (b1) (separation step), a known method such as filtration using any filter or centrifugation can be employed.

Step (b2) aims at washing a trace amount of impurities attached to the solid precipitates with a solvent after the filtration of the solid. In order to carry out Step (b2) (washing step), selection of the solvent used for washing is an important factor. In general, a solvent used for washing such crystalline organic matters may be substantially any solvent as long as it is inert to the compound of interest and its power to dissolve the compound of interest is low. In the method of this embodiment, however, a solvent that is capable of dissolving water for 2 wt % or more, that has no active hydroxy group and that does not dissolve 2-aminoethyl methacrylate hydrochloride for more than 1 wt % is preferable. While specific examples of the solvent include various ketones represented by Formula (4) or (5), tetrahydrofuran and dioxane (for example, 1,4-dioxane), a ketone represented by Formula (4) or (5) is preferably used as the above-described solvent. While specific examples of preferably used ketone include acetone, methyl ethyl ketone, methyl propyl ketone, methyl isobutyl ketone, methyl isopropyl ketone, diisobutyl ketone, cyclopentanone and cyclohexanone, it is more preferable to use acetone, methyl ethyl ketone or methyl isobutyl ketone, and most preferable to use methyl ethyl ketone or methyl isobutyl ketone considering availability and easiness of distillation recovery. Furthermore, the same compound as a ketone represented by General formula (4) or (5) used for synthesizing the so-called Schiff base, i.e., a compound represented by Formula (6) or (7), obtained by reacting with 2-aminoethanol can most favorably be used as the washing solvent so that there will be no need to separate the ketone generated in the deprotection/neutralization reaction from the washing solvent.

Step (b3) is a drying step in which the solvent is vaporized by drying the washed solid precipitate. In the method of this embodiment, it is important to carry out Step (b3) (drying step for removing the solvent). This is because if 2-aminoethyl methacrylate hydrochloride of interest represented by Formula (3) and the solvent coexist, the compound of interest is partially liquefied and provides a reaction field that causes polymerization of the compound of interest, thereby lowering the purity. While any known method can be used as the drying method, drying under reduced pressure is effective. The content of the solvent contained in the dried solid precipitate obtained via Step (b3) is preferably 1 wt % or less.

In addition, in the method of this embodiment, it is effective to use a polymerization inhibitor in order to suppress the polymerization reaction. Specifically, a polymerization inhibitor may be used to suppress the polymerization reaction in the deprotection/neutralization reaction step in which the ketimine compound of 2-aminoethyl methacrylate represented by Formula (1) or (2) is reacted with water and hydrogen chloride to obtain 2-aminoethyl methacrylate hydrochloride represented by Formula (3), the separation step (Step (b1)), the washing step (Step (b2)) and/or the drying step (Step (b3)). There are various aspects in which a polymerization inhibitor used, such as aspects in which a polymerization inhibitor is added to a raw material or an organic solvent used in the deprotection/neutralization reaction, or to a solvent used in the step of washing the compound of interest. Any of these aspects are effective and can be used in the method of this embodiment, and it should appropriately be determined taking the boiling point, the melting point, the solubility or else of the polymerizable compound to be generated into account. Among the above-mentioned aspects, if a polymerization inhibitor is mixed with a solvent used for washing in the washing step (Step (b2)), production of a polymer as a by-product can effectively be suppressed.

The type of the polymerization inhibitor is not particularly limited, and any known type of them can be used. Specific examples include hydroquinone, p-monomethyl hydroquinone, di-t-butylphenol, diphenylamine, 2,2,6,6-tetramethyl piperidine, phenothiazine, 2,2,6,6-tetramethyl-1-piperidinoxy-4-ol, oxygen and nitric oxide. Among them, hydroquinone and p-monomethyl hydroquinone are preferable, which may be used in combination.

If a polymerization inhibitor is to be mixed with water and an organic solvent used for the deprotection/neutralization reaction, the proportion of the polymerization inhibitor to water and the organic solvent used for the deprotection/neutralization reaction is preferably 0.0001-1 wt %.

If the polymerization inhibitor is mixed with the solvent used for washing in the washing step, the proportion of the polymerization inhibitor to the solvent used for washing is preferably 0.0001-1 wt %.

In a method of this embodiment, 2-aminoethyl methacrylate hydrochloride is obtained in a solid form with a high yield, and also the resulting 2-aminoethyl methacrylate hydrochloride has a less impurity content and a high purity.

The yield of 2-aminoethyl methacrylate hydrochloride represented by Formula (3) obtained by the method of this embodiment is 65% or higher. The yield is preferably 75% or higher, and more preferably 80% or higher. This yield refers to the weight fraction of the actual yield achieved by the production method of the embodiment to the theoretical yield of 2-aminoethyl methacrylate hydrochloride calculated from the weight of the ketimine compound of 2-aminoethyl methacrylate represented by Formula (1) or (2) as the reaction raw material.

The purity of 2-aminoethyl methacrylate hydrochloride represented by Formula (3) obtained by the production method of the embodiment is 88% or higher. The purity is preferably 95% or higher and more preferably 98% or higher. This purity refers to a weight fraction of the weight of 2-aminoethyl methacrylate hydrochloride represented by Formula (3) to the weight of the resulting crystals. The amount of 2-aminoethyl methacrylate hydrochloride represented by Formula (3) in the crystals was analyzed by liquid chromatography (column DE413-L from Shodex, 20 mM phosphoric acid-acetonitrile solution (6: 4/vol) as an eluent, RI detector).

EXAMPLES

Hereinafter, the present invention will be described specifically by way of examples. The scope of present invention, however, should not be limited to these examples.

Synthesis Example 1

(Ketimination step)

100.0 g (1.6 mol) of 2-aminoethanol, 443 g (4.4 mol) of methyl isobutyl ketone and 84 g (1.0 mol) of cyclohexane were fed into to a three-neck flask (internal volume: 1000 ml) that was equipped with a magnetic stirrer, a rectifying column (inner diameter: 25 mmφ) packed with 6-mm McMahon packing to a height of 300 mm, a Dean-Stark trap and a reflux condenser, which was heated at a kettle liquid temperature of 90.7-105.9° C. under reflux to synthesize ketimine while draining water accumulated in the Dean-Stark trap from the system. Two hours later, the conversion rate of 2-aminoethanol was 100% while the yield of 2-aminoethanol methyl isobutyl ketimine was 99%.

(Transesterification Step)

The excessive methyl isobutyl ketone and cyclohexane were distilled away from the resulting reaction solution by distillation under reduced pressure. To the remaining kettle liquid, 20.1 g of zinc acetylacetone complex, 317 g (3.2 mol) of methyl methacrylate and 0.32 g of p-methoxyphenol were added. The Dean-Stark trap was replaced with a general distillation head (that was capable of adjusting the reflux amount) to carry out transesterification reaction by heating at a kettle liquid temperature of 107.3-126.4° C. under reflux. The by-product methanol was drained from the system as an azeotropic mixture of methanol and methyl methacrylate. As a polymerization prevention measure, a 1% p-methoxyphenol-methyl methacrylate solution was supplied from the top of the rectifying column at 0.8 g/hour while air was supplied to the reaction solution at 6 ml/min. Five hours later, the reaction solution was analyzed by gas chromatography, where the conversion rate of 2-aminoethanol methyl isobutyl ketimine was 100%. The yield of 2-aminoethyl methacrylate methyl isobutyl ketimine was 62% on the basis of the fed 2-aminoethanol. The resulting reaction solution was subjected to distillation under reduced pressure to first distill the excessive methyl methacrylate away, and then to separate the product, 2-aminoethyl methacrylate methyl isobutyl ketimine. The boiling point of 2-aminoethyl methacrylate methyl isobutyl ketimine was 110° C./0.53 kPa and the total yield of the fraction having a gas chromatography purity of 90% or higher was 146 g (recovery rate: 69%).

Synthesis Example 2

(Ketimination step)

49.0 g (0.80 mol) of 2-aminoethanol, 173 g (2.4 mol) of methyl ethyl ketone and 162 g (1.9 mol) of hexane were fed into to a three-neck flask (internal volume: 1000 ml) that was equipped with a magnetic stirrer, a Dean-Stark trap, a rectifying column (inner diameter: 25 mmφ) packed with 6-mm McMahon packing to a height of 300 mm and a reflux condenser, which was heated at a kettle liquid temperature of 63.7-69.8° C. under reflux to synthesize ketimine while draining water accumulated in the Dean-Stark trap from the system. Six hours later, the conversion rate of 2-aminoethanol was 100% while the yield of 2-aminoethanol methyl ethyl ketimine was 99%.

(Transesterification Step)

The excessive methyl ethyl ketone and hexane were distilled away from the resulting reaction solution. To the remaining kettle liquid, 10.6 g of zinc acetylacetone complex, 0.16 g of p-methoxyphenol and 160 g (1.6 mol) of methyl methacrylate were added. The Dean-Stark trap was replaced with a general distillation head (that was capable of adjusting the reflux amount) to carry out transesterification reaction by heating at a kettle liquid temperature of 97.9-113.9° C. under reflux. The by-product methanol was drained from the system as an azeotropic mixture of methanol and methyl methacrylate. As a polymerization prevention measure, a 4% p-methoxyphenol-methyl methacrylate solution was supplied from the top of the rectifying column at 2 g/hour while air was supplied to the reaction solution at 10 ml/min. Three hours later, the reaction solution was analyzed by gas chromatography, where the conversion rate of 2-aminoethanol methyl ethyl ketimine was 96%. The yield of 2-aminoethyl methacrylate methyl ethyl ketimine was 45% on the basis of the fed 2-aminoethanol. The resulting reaction solution was subjected to distillation under reduced pressure to first distill the excessive methyl methacrylate away, and then to separate the product, 2-aminoethyl methacrylate methyl ethyl ketimine. The boiling point of 2-aminoethyl methacrylate methyl ethyl ketimine was 86.1° C./0.47 kPa and the total yield of the fraction having a gas chromatography purity of 90% or higher was 44 g (recovery rate: 67%).

Example 1

770 g (7.7 mol, containing 200 ppm of water) of methyl isobutyl ketone and 16.1 g (0.894 mol) of water were fed into a three-neck flask (internal volume: 2000 ml) that was equipped with a stirring blade and a dropping tube, and cooled in a methanol-ice bath. The total amount of the fed water was 0.903 mol including the water contained in methyl isobutyl ketone. To this, 32.5 g (0.890 mol) of hydrogen chloride gas was supplied with stirring and 181 g (0.858 mol) of 2-aminoethyl methacrylate methyl isobutyl ketimine obtained in Synthesis example 1 was dropped at the same time by spending 40 minutes. Here, the temperature in the system was maintained at 0° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 20° C. in a water bath for 23 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.05 in equivalent ratio. Following maturation, the compound of interest, i.e., 2-aminoethyl methacrylate hydrochloride, was precipitated in a large amount as white crystals in the system. These white crystals were filtrated with a glass filter, washed with 400 g of methyl isobutyl ketone five times and thereafter dried under reduced pressure, thereby obtaining 139 g of 2-aminoethyl methacrylate hydrochloride with a purity of 99.4%. The isolation yield was 97% on the basis of 2-aminoethyl methacrylate methyl isobutyl ketimine.

Example 2

195 g (0.924 mol) of 2-aminoethyl methacrylate methyl isobutyl ketimine obtained in Synthesis example 1, 770 g (7.7 mol, containing 88 ppm of moisture) of methyl isobutyl ketone and 17.4 g (0.967 mol) of water were fed into a three-neck flask (internal volume: 2000 ml) that was equipped with a stirring blade and a dropping tube, and cooled in ice water. Here, the total amount of the fed water was 0.970 mol including the water contained in methyl isobutyl ketone. To this, 35.1 g (0.962 mol) of hydrogen chloride gas was supplied by spending 60 minutes with stirring and maintaining the temperature at 20° C. or lower. Once the supply was completed, the resultant was subjected to maturation with stirring in a 30° C. water bath for 6 hours. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.05 in equivalent ratio. Following maturation, the compound of interest, i.e., 2-aminoethyl methacrylate hydrochloride, was precipitated in a large amount as white crystals in the system. These white crystals were filtrated with a glass filter, washed with 300 g of methyl isobutyl ketone five times and thereafter dried under reduced pressure, thereby obtaining 148 g of 2-aminoethyl methacrylate hydrochloride with a purity of 99.0%. The isolation yield was 96% on the basis of 2-aminoethyl methacrylate methyl isobutyl ketimine.

Example 3

770 g (7.7 mol, containing 200 ppm of moisture) of methyl isobutyl ketone and 17.1 g (0.950 mol) of water were fed into a three-neck flask (internal volume: 2000 ml) that was equipped with a stirring blade and a dropping tube, and cooled in a methanol-ice bath. Here, the total amount of the fed water was 0.959 mol including the water contained in methyl isobutyl ketone. To this, 40.3 g (1.10 mol) of hydrogen chloride gas was supplied with stirring, and 193 g (0.915 mol) of 2-aminoethyl methacrylate methyl isobutyl ketimine obtained in Synthesis example 1 was dropped at the same time by spending 40 minutes. Here, the temperature in the system was maintained at 0° C. or lower, and the ratio of the accumulated supply amount of hydrogen chloride gas to the accumulated supply amount of 2-aminoethyl methacrylate methyl isobutyl ketimine was controlled to keep 1.2/1.0 in equivalent ratio from the starting point of mixing 2-aminoethyl methacrylate methyl isobutyl ketimine and hydrogen chloride gas to the end point of the mixing. At the end of the addition, the resultant was allowed to mature at 20° C. in a water bath for 93 hours with stirring. The ratio of hydrogen chloride to 2-aminoethyl methacrylate methyl isobutyl ketimine subjected to the reaction was 1.2 in equivalent ratio while the ratio of water to 2-aminoethyl methacrylate methyl isobutyl ketimine was 1.05 in equivalent ratio. Following maturation, the compound of interest, i.e., 2-aminoethyl methacrylate hydrochloride, was precipitated in a large amount as white crystals in the system. These white crystals were filtrated with a glass filter, washed with 400 g of methyl isobutyl ketone five times and thereafter dried under reduced pressure, thereby obtaining 136 g of 2-aminoethyl methacrylate hydrochloride with a purity of 98.9%. The isolation yield was 89% on the basis of 2-aminoethyl methacrylate methyl isobutyl ketimine. The conversion rate after the 23 hours maturation was 81% and the conversion rate after the 93 hours maturation was 97%. The term "conversion rate" refers to a proportion of the consumed 2-aminoethyl methacrylate methyl isobutyl ketimine.

Example 4

770 g (7.7 mol, containing 200 ppm of water) of methyl isobutyl ketone and 17.1 g (0.950 mol) of water were fed into a three-neck flask (internal volume: 2000 ml) that was equipped with a stirring blade and a dropping tube, and cooled in a methanol-ice bath. Here, the total amount of the fed water was 0.959 mol including the water contained in methyl isobutyl ketone. To this, 50.4 g (1.38 mol) of hydrogen chloride gas was supplied with stirring, and 193 g (0.915 mol) of 2-aminoethyl methacrylate methyl isobutyl ketimine obtained in Synthesis example 1 was dropped at the same time by spending 40 minutes. Here, the temperature in the system was maintained at 0° C. or lower, and the ratio of the accumulated supply amount of hydrogen chloride gas to the accumulated supply amount of 2-aminoethyl methacrylate methyl isobutyl ketimine was controlled to keep 1.5/1.0 in equivalent ratio from the starting point of mixing 2-aminoethyl methacrylate methyl isobutyl ketimine and hydrogen chloride gas to the end point of the mixing. At the end of the addition, the resultant was allowed to mature at 20° C. in a water bath for 182 hours with stirring. The ratio of hydrogen chloride to 2-aminoethyl methacrylate methyl isobutyl ketimine subjected to the reaction was 1.5 in equivalent ratio while the ratio of water to 2-aminoethyl methacrylate methyl isobutyl ketimine was 1.05 in equivalent ratio. Following maturation, the compound of interest, i.e., 2-aminoethyl methacrylate hydrochloride, was precipitated in a large amount as white crystals in the system. These white crystals were filtrated with a glass filter, washed with 400 g of methyl isobutyl ketone five times and thereafter dried under reduced pressure, thereby obtaining 112 g of 2-aminoethyl methacrylate hydrochloride with a purity of 96.5%. The isolation yield was 71% on the basis of 2-aminoethyl methacrylate methyl isobutyl ketimine. Here, the conversion rate after the 24 hours maturation was 60% while the conversion rate after the 182 hours maturation was 90%. The term "conversion rate" refers to a proportion of the consumed 2-aminoethyl methacrylate methyl isobutyl ketimine.

Example 5

770 g (7.7 mol, containing 200 ppm of water) of methyl isobutyl ketone and 15.5 g (0.861 mol) of water were fed into a three-neck flask (internal volume: 2000 ml) that was equipped with a stirring blade and a dropping tube, and cooled in a methanol-ice bath. Here, the total amount of the fed water was 0.870 mol including the water contained in methyl isobutyl ketone. To this, 32.6 g (0.893 mol) of hydrogen chloride gas was supplied with stirring, and 181 g (0.858 mol) of 2-aminoethyl methacrylate methyl isobutyl ketimine obtained in Synthesis example 1 was dropped at the same time by spending 40 minutes. Here, the temperature in the system was maintained at 0° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 20° C. in a water bath for 23 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.01 in equivalent ratio. Following maturation, the compound of interest, i.e., 2-aminoethyl methacrylate hydrochloride, was precipitated in a large amount as white crystals in the system. These white crystals were filtrated with a glass filter, washed with 400 g of methyl isobutyl ketone five times and thereafter dried under reduced pressure, thereby obtaining 140 g of 2-aminoethyl methacrylate hydrochloride with a purity of 99.1%. The isolation yield was 98% on the basis of 2-aminoethyl methacrylate methyl isobutyl ketimine.

Example 6

770 g (7.7 mol, containing 200 ppm of water) of methyl isobutyl ketone and 19.6 g (1.089 mol) of water were fed into a three-neck flask (internal volume: 2000 ml) that was equipped with a stirring blade and a dropping tube, and cooled in a methanol-ice bath. Here, the total amount of the fed water was 1.098 mol including the water contained in methyl isobutyl ketone. To this, while stirring, 34.7 g (0.951 mol) of hydrogen chloride gas was supplied, and 193 g (0.915 mol) of 2-aminoethyl methacrylate methyl isobutyl ketimine obtained in Synthesis example 1 was dropped at the same time by spending 40 minutes. Here, the temperature in the system was maintained at 0° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 20° C. in a water bath for 23 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.2 in equivalent ratio. Following maturation, the compound of interest, i.e., 2-aminoethyl methacrylate hydrochloride, was precipitated in a large amount as white crystals in the system. These white crystals were filtrated with a glass filter, washed with 400 g of methyl isobutyl ketone five times and thereafter dried under reduced pressure, thereby obtaining 145 g of 2-aminoethyl methacrylate hydrochloride with a purity of 99.2%. The isolation yield was 95% on the basis of 2-aminoethyl methacrylate methyl isobutyl ketimine.

Example 7

770 g (7.7 mol, containing 200 ppm of water) of methyl isobutyl ketone and 24.5 g (1.361 mol) of water were fed into a three-neck flask (internal volume: 2000 ml) that was equipped with a stirring blade and a dropping tube, and cooled in a methanol-ice bath. Here, the total amount of the fed water was 1.370 mol including the water contained in methyl isobutyl ketone. To this, 34.7 g (0.951 mol) of hydrogen chloride gas was supplied with stirring, and 193 g (0.915 mol) of 2-aminoethyl methacrylate methyl isobutyl ketimine obtained in Synthesis example 1 was dropped at the same time by spending 40 minutes. Here, the temperature in the system was maintained at 0° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 20° C. in a water bath for 23 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.5 in equivalent ratio. Following maturation, the compound of interest, i.e., 2-aminoethyl methacrylate hydrochloride, was precipitated in a large amount as white crystals in the system. These white crystals were filtrated with a glass filter, washed with 400 g of methyl isobutyl ketone five times and thereafter dried under reduced pressure, thereby obtaining 148 g of 2-aminoethyl methacrylate hydrochloride with a purity of 95.3%. The isolation yield was 93% on the basis of 2-aminoethyl methacrylate methyl isobutyl ketimine.

Example 8

770 g (7.7 mol, containing 200 ppm of water) of methyl isobutyl ketone and 32.8 g (1.822 mol) of water were fed into a three-neck flask (internal volume: 2000 ml) that was equipped with a stirring blade and a dropping tube, and cooled in a methanol-ice bath. Here, the total amount of the fed water was 1.831 mol including the water contained in methyl isobutyl ketone. To this, 34.7 g (0.951 mol) of hydrogen chloride gas was supplied with stirring, and 193 g (0.915 mol) of 2-aminoethyl methacrylate methyl isobutyl ketimine obtained in Synthesis example 1 was dropped at the same time by spending 40 minutes. Here, the temperature in the system was maintained at 0° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 20° C. in a water bath for 23 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 2.0 in equivalent ratio. Following maturation, the compound of interest, i.e., 2-aminoethyl methacrylate hydrochloride, was precipitated in a large amount as white crystals in the system. These white crystals were filtrated with a glass filter, washed with 400 g of methyl isobutyl ketone five times and thereafter dried under reduced pressure, thereby obtaining 128 g of 2-aminoethyl methacrylate hydrochloride with a purity of 89.2%. The isolation yield was 75% on the basis of 2-aminoethyl methacrylate methyl isobutyl ketimine.

Example 9

770 g (7.7 mol, containing 200 ppm of water) of methyl isobutyl ketone and 17.1 g (0.95 mol) of water were fed into a three-neck flask (internal volume: 2000 ml) that was equipped with a stirring blade and a dropping tube, and cooled in a methanol-ice bath. Here, the total amount of the fed water was 0.96 mol including the water contained in methyl isobutyl ketone. To this, 34.7 g (0.95 mol) of hydrogen chloride gas was supplied with stirring, and 193 g (0.91 mol) of 2-aminoethyl methacrylate methyl isobutyl ketimine obtained in Synthesis example 1 was dropped at the same time by spending 40 minutes. Here, the temperature in the system was maintained at 0° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 30° C. in a water bath for 15 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.05 in equivalent ratio. Following maturation, the compound of interest, i.e., 2-aminoethyl methacrylate hydrochloride, was precipitated in a large amount as white crystals in the system. These white crystals were filtrated with a glass filter, washed with 400 g of methyl isobutyl ketone five times and thereafter dried under reduced pressure, thereby obtaining 146 g of 2-aminoethyl methacrylate hydrochloride with a purity of 99.4%. The isolation yield was 96% on the basis of 2-aminoethyl methacrylate methyl isobutyl ketimine.

Example 10

770 g (7.7 mol, containing 200 ppm of water) of methyl isobutyl ketone and 17.3 g (0.96 mol) of water were fed into a three-neck flask (internal volume: 2000 ml) that was equipped with a stirring blade and a dropping tube, and cooled in a methanol-ice bath. Here, the total amount of the fed water was 0.97 mol including the water contained in methyl isobutyl ketone. To this, 34.9 g (0.96 mol) of hydrogen chloride gas was supplied with stirring, and 194 g (0.92 mol) of 2-aminoethyl methacrylate methyl isobutyl ketimine obtained in Synthesis example 1 was dropped at the same time by spending 40 minutes. Here, the temperature in the system was maintained at 0° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 40° C. in a water bath for 7 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.05 in equivalent ratio. Following maturation, the compound of interest, i.e., 2-aminoethyl methacrylate hydrochloride, was precipitated in a large amount as white crystals in the system. These white crystals were filtrated with a glass filter, washed with 400 g of methyl isobutyl ketone five times and thereafter dried under reduced pressure, thereby obtaining 146 g of 2-aminoethyl methacrylate hydrochloride with a purity of 98.0%. The isolation yield was 94% on the basis of 2-aminoethyl methacrylate methyl isobutyl ketimine.

Example 11

770 g (7.7 mol, containing 200 ppm of water) of methyl isobutyl ketone and 16.1 g (0.89 mol) of water were fed into a three-neck flask (internal volume: 2000 ml) that was equipped with a stirring blade and a dropping tube, and cooled in a methanol-ice bath. Here, the total amount of the fed water was 0.90 mol including the water contained in methyl isobutyl ketone. To this, 32.5 g (0.89 mol) of hydrogen chloride gas was supplied with stirring, and 181 g (0.86 mol) of 2-aminoethyl methacrylate methyl isobutyl ketimine obtained in Synthesis example 1 was dropped at the same time by spending 40 minutes. Here, the temperature in the system was maintained at 20° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 20° C. in a water bath for 23 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.05 in equivalent ratio. Following maturation, the compound of interest, i.e., 2-aminoethyl methacrylate hydrochloride, was precipitated in a large amount as white crystals in the system. These white crystals were filtrated with a glass filter, washed with 400 g of methyl isobutyl ketone five times and thereafter dried under reduced pressure, thereby obtaining 133 g of 2-aminoethyl methacrylate hydrochloride with a purity of 99.8%. The isolation yield was 93% on the basis of 2-aminoethyl methacrylate methyl isobutyl ketimine. Furthermore, on the glass filter used for filtrating 2-aminoethyl methacrylate hydrochloride, what appeared to be a polymer generated by moisture absorption/gelation of 2-aminoethyl methacrylate hydrochloride was confirmed.

Example 12

770 g (7.7 mol, containing 200 ppm of water) of methyl isobutyl ketone and 16.1 g (0.89 mol) of water were fed into a three-neck flask (internal volume: 2000 ml) that was equipped with a stirring blade and a dropping tube, and cooled in a methanol-ice bath. Here, the total amount of the fed water was 0.90 mol including the water contained in methyl isobutyl ketone. To this, 32.5 g (0.89 mol) of hydrogen chloride gas was supplied with stirring, and 181 g (0.86 mol) of 2-aminoethyl methacrylate methyl isobutyl ketimine obtained in Synthesis example 1 was dropped at the same time by spending 40 minutes. Here, the temperature in the system was maintained at 30° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 20° C. in a water bath for 23 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.05 in equivalent ratio. Following maturation, the compound of interest, i.e., 2-aminoethyl methacrylate hydrochloride, was precipitated in a large amount as white crystals in the system. These white crystals were filtrated with a glass filter, washed with 400 g of methyl isobutyl ketone five times and thereafter dried under reduced pressure, thereby obtaining 126 g of 2-aminoethyl methacrylate hydrochloride with a purity of 99.4%. The isolation yield was 88% on the basis of 2-aminoethyl methacrylate methyl isobutyl ketimine.

Example 13

770 g (7.7 mol, containing 200 ppm of water) of methyl isobutyl ketone and 16.1 g (0.89 mol) of water were fed into a three-neck flask (internal volume: 2000 ml) that was equipped with a stirring blade and a dropping tube, and cooled in a methanol-ice bath. Here, the total amount of the fed water was 0.90 mol including the water contained in methyl isobutyl ketone. To this, 32.5 g (0.89 mol) of hydrogen chloride gas was supplied with stirring, and 181 g (0.86 mol) of 2-aminoethyl methacrylate methyl isobutyl ketimine obtained in Synthesis example 1 was dropped at the same time by spending 40 minutes. Here, the temperature in the system was maintained at 57° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 20° C. in a water bath for 23 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.05 in equivalent ratio. Following maturation, the compound of interest, i.e., 2-aminoethyl methacrylate hydrochloride, was precipitated in a large amount as white crystals in the system. These white crystals were filtered with a glass filter, washed with 400 g of methyl isobutyl ketone five times and thereafter dried under reduced pressure, thereby obtaining 116 g of 2-aminoethyl methacrylate hydrochloride with a purity of 96.0%. The isolation yield was 78% on the basis of 2-aminoethyl methacrylate methyl isobutyl ketimine.

Example 14

770 g (7.7 mol, containing 200 ppm of water) of methyl isobutyl ketone and 16.1 g (0.89 mol) of water were fed into a three-neck flask (internal volume: 2000 ml) that was equipped with a stirring blade and a dropping tube, and cooled in a methanol-ice bath. Here, the total amount of the fed water was 0.90 mol including the water contained in methyl isobutyl ketone. To this, 32.5 g (0.89 mol) of hydrogen chloride gas was supplied with stirring, and 181 g (0.86 mol) of 2-aminoethyl methacrylate methyl isobutyl ketimine obtained in Synthesis example 1 was dropped at the same time by spending 40 minutes. Here, the temperature in the system was maintained at 40° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 40° C. in a water bath for 7 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.05 in equivalent ratio. Following maturation, the compound of interest, i.e., 2-aminoethyl methacrylate hydrochloride, was precipitated in a large amount as white crystals in the system. These white crystals were filtered with a glass filter, washed with 400 g of methyl isobutyl ketone five times and thereafter dried under reduced pressure, thereby obtaining 137 g of 2-aminoethyl methacrylate hydrochloride with a purity of 98.0%. The isolation yield was 94% on the basis of 2-aminoethyl methacrylate methyl isobutyl ketimine.

Example 15

770 g (7.7 mol, containing 200 ppm of water) of methyl isobutyl ketone and 16.1 g (0.89 mol) of water were fed into a three-neck flask (internal volume: 2000 ml) that was equipped with a stirring blade and a dropping tube, and cooled in a methanol-ice bath. Here, the total amount of the fed water was 0.90 mol including the water contained in methyl isobutyl ketone. To this, 32.5 g (0.89 mol) of hydrogen chloride gas was supplied with stirring, and 181 g (0.86 mol) of 2-aminoethyl methacrylate methyl isobutyl ketimine obtained in Synthesis example 1 was dropped at the same time by spending 40 minutes. Here, the temperature in the system was maintained at 20° C. or lower, and the ratio of the accumulated supply amount of hydrogen chloride gas to the accumulated supply amount of 2-aminoethyl methacrylate methyl isobutyl ketimine was controlled to keep 1.04/1.00 in equivalent ratio from the starting point of mixing 2-aminoethyl methacrylate methyl isobutyl ketimine and hydrogen chloride gas to the end point of the mixing. At the end of the addition, the resultant was allowed to mature at 20° C. in a water bath for 23 hours with stirring. The ratio of hydrogen chloride to 2-aminoethyl methacrylate methyl isobutyl ketimine subjected to the reaction was 1.04 in equivalent ratio while the ratio of water to 2-aminoethyl methacrylate methyl isobutyl ketimine was 1.05 in equivalent ratio. Following maturation, the compound of interest, i.e., 2-aminoethyl methacrylate hydrochloride, was precipitated in a large amount as white crystals in the system. These white crystals were filtered with a glass filter, washed with 400 g of methyl isobutyl ketone containing 0.1 wt % p-monomethyl hydroquinone five times and thereafter dried under reduced pressure, thereby obtaining 130 g of 2-aminoethyl methacrylate hydrochloride with a purity of 99.7%. The isolation yield was 91% on the basis of 2-aminoethyl methacrylate methyl isobutyl ketimine. Furthermore, on the glass filter used for filtrating 2-aminoethyl methacrylate hydrochloride, what appeared to be a polymer generated by moisture absorption/gelation of 2-aminoethyl methacrylate hydrochloride was not confirmed.

Example 16

3017 g (41.9 mol, containing 200 ppm of water) of tetrahydrofuran and 81.3 g (4.52 mol) of water were fed into a three-neck flask (internal volume: 5000 ml) that was equipped with a stirring blade and a dropping tube, and cooled in a methanol-ice bath. To this, 165.3 g (4.53 mol) of hydrogen chloride gas was supplied with stirring and maintaining the temperature at 0° C. or lower. Subsequently, 689 g (3.76 mol) of 2-aminoethyl methacrylate methyl ethyl ketimine obtained in Synthesis example 2 was dropped by spending 40 minutes while maintaining the temperature at 0° C. or lower. At the end of dropping, the resultant was allowed to mature at 20° C. in a water bath for 28 hours with stirring. The ratio of hydrogen chloride to 2-aminoethyl methacrylate methyl ethyl ketimine subjected to the reaction was 1.2 in equivalent ratio while the ratio of water to 2-aminoethyl methacrylate methyl ethyl ketimine was 1.2 in equivalent ratio. Following maturation, the precipitated 2-aminoethyl methacrylate hydrochloride was filtrated with a glass filter. The resulting crystals were washed with tetrahydrofuran, and dried under reduced pressure. The yield of 2-aminoethyl methacrylate hydrochloride as the main component was 566 g (with a purity of 98.5%). The isolation yield was 90% on the basis of 2-aminoethyl methacrylate methyl ethyl ketimine.

Example 17

5.63 g of concentrated hydrochloric acid (containing 37 wt % hydrogen chloride) was fed into a three-neck flask (internal volume: 200 ml) that was equipped with a magnetic stirrer and a dropping tube, and cooled in a methanol-ice bath. To this, 4.51 g (0.12 mol) of hydrogen chloride gas was supplied with stirring, and 30.1 g (0.16 mol) of 2-aminoethyl methacrylate methyl ethyl ketimine obtained in Synthesis example 2 was dropped by spending 20 minutes such that both were completely supplied almost at the same time. Here, the temperature in the system was maintained at 5° C. or lower, and the ratio of the accumulated supply amount of hydrogen chloride gas to the accumulated supply amount of 2-aminoethyl methacrylate methyl ethyl ketimine was controlled to keep 3/4 in equivalent ratio from the starting point of mixing 2-aminoethyl methacrylate methyl ethyl ketimine and hydrogen chloride gas (excluding hydrogen chloride contained in concentrated hydrochloric acid) to the end point of the mixing. At the end of the addition, the resultant was allowed to mature at 20° C. in a water bath for 30 minutes with stirring. The ratio of hydrogen chloride to 2-aminoethyl methacrylate methyl ethyl ketimine subjected to the reaction was 1.1 in equivalent ratio while the ratio of water to 2-aminoethyl methacrylate methyl ethyl ketimine was 1.2 in equivalent ratio. Following maturation, the precipitated 2-aminoethyl methacrylate hydrochloride was filtrated with a glass filter. The resulting crystals was washed with 1,4-dioxane, and dried under reduced pressure. The yield of 2-aminoethyl methacrylate hydrochloride as the main component was 24.1 g (with a purity of 99.9%). The isolation yield was 91% on the basis of 2-aminoethyl methacrylate methyl ethyl ketimine.

Example 18

5.63 g of concentrated hydrochloric acid (containing 37 wt % hydrogen chloride) was fed into a three-neck flask (internal volume: 200 ml) that was equipped with a magnetic stirrer and a dropping tube, and cooled in a methanol-ice bath. To this, 4.51 g (0.12 mol) of hydrogen chloride gas was supplied with stirring, 30.1 g (0.16 mol) of 2-aminoethyl methacrylate methyl ethyl ketimine obtained in Synthesis example 2 was dropped by spending 20 minutes such that both were completely supplied almost at the same time. Here, the temperature in the system was maintained at 5° C. or lower, and the ratio of the accumulated supply amount of hydrogen chloride gas to the accumulated supply amount of 2-aminoethyl methacrylate methyl ethyl ketimine was controlled to keep 3/4 in equivalent ratio from the starting point of mixing 2-aminoethyl methacrylate methyl ethyl ketimine and hydrogen chloride gas (excluding hydrogen chloride contained in concentrated hydrochloric acid) to the end point of the mixing. At the end of the addition, the resultant was allowed to mature at 20° C. in a water bath for 30 minutes with stirring. The ratio of hydrogen chloride to 2-aminoethyl methacrylate methyl ethyl ketimine subjected to the reaction was 1.1 in equivalent ratio while the ratio of water to 2-aminoethyl methacrylate methyl ethyl ketimine was 1.2 in equivalent ratio. Following maturation, the precipitated 2-aminoethyl methacrylate hydrochloride was filtrated with a glass filter. The resulting crystals were washed with acetone and dried under reduced pressure. The yield of 2-aminoethyl methacrylate hydrochloride as the main component was 22.6 g (with a purity of 99.9%). The isolation yield was 83% on the basis of 2-aminoethyl methacrylate methyl ethyl ketimine.

Example 19

76.3 g (4.24 mol) of water was fed into a three-neck flask (internal volume: 5000 ml) that was equipped with a stirring blade and a dropping tube, to which 136.3 g (3.73 mol) of hydrogen chloride gas was supplied with stirring, and 648 g (3.54 mol) of 2-aminoethyl methacrylate methyl ethyl ketimine obtained in Synthesis example 2 was dropped at the same time by spending 1.2 hours such that both were completely supplied almost at the same time. Here, the temperature in the system was maintained at 10° C. or lower, and the ratio of the accumulated supply amount of hydrogen chloride gas to the accumulated supply amount of 2-aminoethyl methacrylate methyl ethyl ketimine was controlled to keep 1.05/1.00 in equivalent ratio from the starting point of mixing 2-aminoethyl methacrylate methyl ethyl ketimine and hydrogen chloride gas to the end point of the mixing. At the end of the addition, the resultant was allowed to mature at 10° C. in a water bath for 28 hours with stirring. The ratio of hydrogen chloride to 2-aminoethyl methacrylate methyl ethyl ketimine subjected to the reaction was 1.05 in equivalent ratio while the ratio of water to 2-aminoethyl methacrylate methyl ethyl ketimine was 1.2 in equivalent ratio. Following maturation, 4000 ml of methyl ethyl ketone was added and stirred for 30 minutes, and then 2-aminoethyl methacrylate hydrochloride was filtrated with a glass filter. The resulting crystals were washed with methyl ethyl ketone and dried under reduced pressure. The yield of 2-aminoethyl methacrylate hydrochloride as the main component was 510 g (with a purity of 99.1%). The isolation yield was 86% on the basis of 2-aminoethyl methacrylate methyl ethyl ketimine.

Example 20

98.4 g (0.54 mol) of 2-aminoethyl methacrylate methyl ethyl ketimine obtained in Synthesis example 2, 324 g (4.5 mol, containing 525 ppm water) of methyl ethyl ketone and 10.0 g (0.55 mol) of water were fed into a three-neck flask (internal volume: 1000 ml) that was equipped with a stirring blade and a dropping tube, and cooled in ice water. Here, the total amount of the fed water was 0.57 mol including the water contained in methyl ethyl ketone. To this, 20.3 g (0.56 mol) of hydrogen chloride gas was supplied by spending 30 minutes with stirring and maintaining at 20° C. or lower. At the end of the supply, the resultant was allowed to mature in a water bath at 30° C. for 6 hours with stirring. The ratio of hydrogen chloride to 2-aminoethyl methacrylate methyl ethyl ketimine subjected to the reaction was 1.04 in equivalent ratio while the ratio of water to 2-aminoethyl methacrylate methyl ethyl ketimine was 1.05 in equivalent ratio. Following maturation, the compound of interest, i.e., 2-aminoethyl methacrylate hydrochloride, was precipitated in a large amount as white crystals in the system. These white crystals were filtrated with a glass filter, washed with 200 g of methyl ethyl ketone five times and dried under reduced pressure, thereby obtaining 75 g of 2-aminoethyl methacrylate hydrochloride with a purity of 99.7%. The isolation yield was 84% on the basis of 2-aminoethyl methacrylate methyl ethyl ketimine.

Example 21

2454 g (34.1 mol, containing 525 ppm of water) of methyl ethyl ketone and 74.5 g (4.139 mol) of water were fed into a three-neck flask (internal volume: 5000 ml) that was equipped with a stirring blade and a dropping tube, and cooled in a methanol-ice bath. Here, the total amount of the fed water was 4.210 mol including the water contained in methyl ethyl ketone. To this, 152.3 g (4.173 mol) of hydrogen chloride gas was supplied with stirring and 734 g (4.011 mol) of 2-aminoethyl methacrylate methyl ethyl ketimine obtained in Synthesis example 2 was dropped at the same time by spending 60 minutes. Here, the temperature in the system was maintained at 20° C. or lower, and the ratio of the accumulated supply amount of hydrogen chloride gas to the accumulated supply amount of 2-aminoethyl methacrylate methyl ethyl ketimine was controlled to keep 1.04/1.00 in equivalent ratio from the starting point of mixing 2-aminoethyl methacrylate methyl ethyl ketimine and hydrogen chloride gas to the end point of the mixing. At the end of the addition, the resultant was allowed to mature at 30° C. in a water bath for 6 hours with stirring. The ratio of hydrogen chloride to 2-aminoethyl methacrylate methyl ethyl ketimine subjected to the reaction was 1.04 in equivalent ratio while the ratio of water to 2-aminoethyl methacrylate methyl ethyl ketimine was 1.05 in equivalent ratio. Following maturation, the compound of interest, i.e., 2-aminoethyl methacrylate hydrochloride, was precipitated in a large amount as white crystals in the system. These white crystals were filtrated with a glass filter, washed with 800 g of methyl ethyl ketone five times and dried under reduced pressure, thereby obtaining 617 g of 2-aminoethyl methacrylate hydrochloride with a purity of 99.9%. The isolation yield was 93% on the basis of 2-aminoethyl methacrylate methyl ethyl ketimine.

Comparative Example 1

83.8 g of concentrated hydrochloric acid (containing 36.3 wt % hydrogen chloride) was fed into a three-neck flask (internal volume: 500 ml) that was equipped with a magnetic stirrer and a dropping tube, and cooled in ice bath. To this, 147 g (0.803 mol) of 2-aminoethyl methacrylate methyl ethyl ketimine obtained in Synthesis example 2 was dropped with stirring by spending 2 hours. The ratio of hydrogen chloride to 2-aminoethyl methacrylate methyl ethyl ketimine subjected to the reaction was 1.04 in equivalent ratio while the ratio of water to 2-aminoethyl methacrylate methyl ethyl ketimine was 3.69 in equivalent ratio. At the end of dropping, the resultant was allowed to mature at 20° C. in a water bath for 2 hours with stirring, to which 832 g of tetrahydrofuran was added and left to stand at 20° C. for 15 hours. At this point, no precipitation of crystal was confirmed, and solid 2-aminoethyl methacrylate hydrochloride was not obtained.

The invention claimed is:
1. A method for producing 2-aminoethyl methacrylate hydrochloride, comprising (A) reacting a ketimine compound of 2-aminoethyl methacrylate represented by Formula (1) or (2) below,

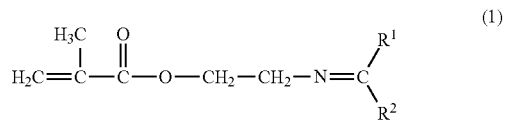

wherein, in Formula (1), $R^1$ and $R^2$ each independently represent an alkyl group or an aryl group with a carbon number of 1-12,

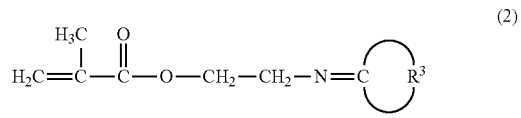

wherein, in Formula (2), $R^3$ represents a bivalent hydrocarbon group with a carbon number of 3-10 that forms a ring with a carbon atom to which it binds, and may partly have a double bond,
with water and hydrogen chloride to obtain a mixture containing 2-aminoethyl methacrylate hydrochloride represented by Formula (3) below,

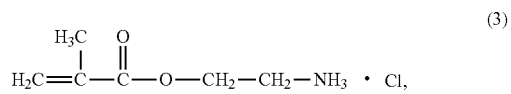

wherein, in (A), the ratio of the whole amount of hydrogen chloride to the whole amount of the ketimine compound of 2-aminoethyl methacrylate is in a range of 1.0-1.5 in equivalent ratio, and the ratio of the whole amount of water to the whole amount of the ketimine compound of 2-aminoethyl methacrylate is in a range of 1.0-2.0 in equivalent ratio.
2. The method for producing 2-aminoethyl methacrylate hydrochloride according to claim 1, wherein $R^1$ and $R^2$ in Formula (1) above each independently represent an alkyl group with a carbon number of 1-4.
3. The method for producing 2-aminoethyl methacrylate hydrochloride according to claim 2, wherein, in Formula (1) above, $R^1$ represents a methyl group and $R^2$ represents an ethyl group or an isobutyl group.
4. The method for producing 2-aminoethyl methacrylate hydrochloride according to claim 3, wherein $R^2$ in Formula (1) above represents an isobutyl group.
5. The method for producing 2-aminoethyl methacrylate hydrochloride according to claim 3, wherein $R^2$ in Formula (1) above represents an ethyl group.
6. The method for producing 2-aminoethyl methacrylate hydrochloride according to claim 1, wherein hydrogen chloride is hydrogen chloride gas.
7. The method for producing 2-aminoethyl methacrylate hydrochloride according to claim 1, wherein the reaction of the ketimine compound of 2-aminoethyl methacrylate represented by Formula (1) with water and hydrogen chloride is carried out such that hydrogen chloride and the ketimine compound are added to the water such that the ratio of the accumulated supply amount of hydrogen chloride to the accumulated supply amount of the ketimine compound of 2-aminoethyl methacrylate is maintained at 1.0 or higher in equivalent ratio throughout the whole period from the starting point of mixing hydrogen chloride with the ketimine compound of 2-aminoethyl methacrylate to the end point of mixing the whole amount of hydrogen chloride.

8. The method for producing 2-aminoethyl methacrylate hydrochloride according to claim 1, wherein the reaction of the ketimine compound of 2-aminoethyl methacrylate with water and hydrogen chloride is carried out in the presence of at least one organic solvent selected from the group consisting of tetrahydrofuran, methyl isobutyl ketone, methyl ethyl ketone, acetone and dioxane.

9. The method for producing 2-aminoethyl methacrylate hydrochloride according to claim 8, wherein the organic solvent is at least one selected from the group consisting of methyl isobutyl ketone and methyl ethyl ketone.

10. The method for producing 2-aminoethyl methacrylate hydrochloride according to claim 8, wherein the organic solvent is used in an amount four times as much as or less than the amount of the ketimine compound of 2-aminoethyl methacrylate represented by Formula (1) or (2) above in weight ratio.

11. The method for producing 2-aminoethyl methacrylate hydrochloride according to claim 1, wherein the temperature in (A) is controlled to lie in a range of −10-60° C. from the starting point of supplying any of hydrogen chloride, ketimine, and water to the reaction vessel to the end point wherein all reactants have been supplied.

12. The method for producing 2-aminoethyl methacrylate hydrochloride according to claim 1, wherein the temperature in (A) is controlled to lie in a range of −10-40° C., once all reactants have been added.

13. The method for producing 2-aminoethyl methacrylate hydrochloride according to claim 1, further comprising (B) which comprises (b1) of separating solid precipitate from the mixture containing 2-aminoethyl methacrylate hydrochloride obtained in (A);
(b2) of washing the solid precipitate with a solvent; and
(b3) of drying the washed solid precipitate.

14. The method for producing 2-aminoethyl methacrylate hydrochloride according to claim 13, wherein the solvent in (b2) is at least one selected from the group consisting of acetone, methyl ethyl ketone, methyl isobutyl ketone, tetrahydrofuran and 1,4-dioxane.

15. The method for producing 2-aminoethyl methacrylate hydrochloride according to claim 13 wherein the solvent in (b2) contains a polymerization inhibitor.

16. The method for producing 2-aminoethyl methacrylate hydrochloride according to claim 1, wherein 2-aminoethyl methacrylate hydrochloride is solid.

* * * * *